United States Patent [19]

Dingwall et al.

[11] 4,384,966

[45] May 24, 1983

[54] PHOSPHORUS SUBSTITUTED 4-METHYLOXETAN-2-ONES, PROCESSES FOR THEIR PREPARATION AND THEIR USE

[75] Inventors: John G. Dingwall, Brooklands; Brian Tuck, Bramhall, both of England

[73] Assignee: Ciba-Geigy Corporation, Ardsley, N.Y.

[21] Appl. No.: 245,576

[22] Filed: Mar. 20, 1981

[30] Foreign Application Priority Data

Mar. 27, 1980 [GB] United Kingdom ............... 8010383

[51] Int. Cl.³ .................. C10M 1/20; C10M 1/26; C10M 1/44; C07D 305/12
[52] U.S. Cl. ......................... 252/46.6; 252/49.8; 204/158 R; 549/222; 549/214
[58] Field of Search .......... 260/343.9, 340.7, 340.9 R; 252/49.8, 46.6; 204/158 R

[56] References Cited

U.S. PATENT DOCUMENTS

| | | | |
|---|---|---|---|
| 2,450,131 | 9/1948 | Hagemeyer | 260/343.9 X |
| 2,585,537 | 2/1952 | Coffman | 260/78.5 |
| 2,675,392 | 4/1954 | Theobald | 260/343.9 |
| 3,432,599 | 3/1969 | Hackmann | 260/343.9 X |
| 3,994,929 | 11/1976 | Allen et al. | 260/343.9 |
| 4,009,152 | 2/1977 | Mormann et al. | 260/343.9 X |
| 4,178,286 | 12/1979 | Wasserman et al. | 260/340.7 X |
| 4,207,417 | 6/1980 | Vofsi et al. | 260/340.7 X |
| 4,230,720 | 10/1980 | Walker | 260/340.7 X |

Primary Examiner—Paul F. Shaver
Attorney, Agent, or Firm—Michael W. Glynn

[57] ABSTRACT

Compounds having the formula

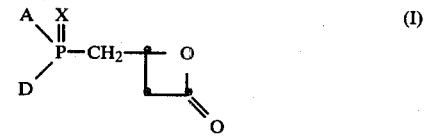

are described, wherein X is oxygen or sulphur or the moiety X is absent and A and D are as defined in claim 1. Compounds I may be prepared by reacting a compound

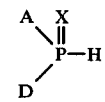

with diketene in the presence of an agent capable of forming free radicals. They are useful as friction modifiers and/or antiwear additives in lubricating oils or for imparting flame-retardancy to natural or synthetic polymers.

14 Claims, No Drawings

PHOSPHORUS SUBSTITUTED 4-METHYLOXETAN-2-ONES, PROCESSES FOR THEIR PREPARATION AND THEIR USE

The present invention relates to new phosphorus substituted 4-methyloxetan-2-ones, processes for their preparation and their use in lubricant compositions or for imparting flame retardancy to natural and synthetic polymers.

According to the present invention there is provided a compound having the general formula I

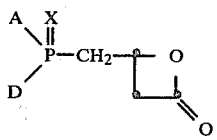

wherein X is oxygen or sulphur or the moiety X is absent; and A and D are the same or different and each is hydrogen, $C_1$-$C_{12}$ straight chain or branched chain alkyl (optionally substituted by one or two halogen atoms or by a cyano, $C_1$-$C_3$ alkoxy, or $C_2$-$C_4$ alkoxycarbonyl), $C_3$-$C_7$ cycloalkyl, $C_7$-$C_{10}$ aralkyl or a phenyl group (optionally substituted by one or two halogen, cyano, $C_1$-$C_3$ alkoxy, $C_2$-$C_4$ alkoxycarbonyl or $C_1$-$C_4$ straight chain or branched chain alkyl groups), the group

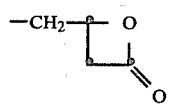

or a group R'O— wherein R' is hydrogen, a $C_1$-$C_{12}$ straight or branched chain alkyl group (optionally substituted by one or two halogen atoms), $C_3$-$C_7$ cycloalkyl, $C_7$-$C_{10}$ aralkyl, a phenyl group (optionally substituted by one or two halogen atoms or $C_1$-$C_4$ straight chain or branched chain alkyl groups), or R' is a trimethylsilyl group; or A and D together with the phosphorus atom to which they are each attached form a 1,3,2-dioxaphospholane ring or a 1,3,2-dioxaphosphorinane ring, each optionally substituted by one or more $C_1$-$C_3$ straight chain or branched chain alkyl; and where R' is hydrogen, the alkali, alkaline earth and amine salts and partial salts thereof; with the proviso that when A is the group R'O— and X is sulphur or absent then D cannot be hydrogen or the group

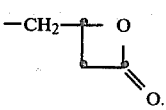

When A and/or D is a $C_1$-$C_{12}$ straight- or branched chain alkyl group, it may e.g. be a methyl, ethyl, n-propyl, isopropyl, n-butyl, sec.-butyl, t-butyl, n-pentyl, n-hexyl, n-heptyl, n-octyl, n-nonyl, n-decyl, n-undecyl or n-dodecyl group.

When A and/or D is an alkyl or phenyl group substituted by halogen atoms, the halogen atom may be fluorine or iodine but is preferably chlorine or bromine. Examples of $C_1$-$C_3$ alkoxy substituents in A and/or D are methoxy, ethoxy, n-propoxy and isopropoxy groups. Alkoxycarbonyl substituents in A and/or D may be e.g. methoxycarbonyl, ethoxycarbonyl, n-propoxycarbonyl and isopropoxycarbonyl groups. $C_1$-$C_4$ Alkyl substituents of phenyl groups A and/or D are e.g. methyl, ethyl, n-propyl, isopropyl and tertiary butyl groups. Cycloalkyl groups A and/or D include cyclopropyl, cyclobutyl, cyclopentyl, cyclohexyl and cycloheptyl groups.

Aralkyl groups A and/or D include benzyl and α,α-dimethylbenzyl groups.

When the group R' consists of or contains a $C_1$-$C_{12}$ alkyl group, a halogen atom, a $C_3$-$C_7$ cycloalkyl group, a $C_7$-$C_{10}$ aralkyl group or a $C_1$-$C_4$ alkyl group, examples of these groups are the same as those given under groups A and/or D.

X is preferably sulphur and especially oxygen, and A is preferably a group —OR' wherein R' is as defined under formula I.

The following Tables 1 to 9 illustrate compounds falling within formula I in which the phosphorus atom is not part of a ring.

It is understood that compounds of the formula I, in which X is oxygen and at least one of A and D is hydrogen, are tautomeric with compounds of formula I where X is absent and at least one of A and D is an OH group.

TABLE 1

X is O, A is —OR', D is —OR'

| A | D |
|---|---|
| —OH | —OH |
| —OH | —OCH$_3$ |
| —OH | —OC$_8$H$_{17}$—n |
| —OCH$_3$ | —OCH$_3$ |
| —OCH$_3$ | —OC$_4$H$_9$—n |
| —OCH$_3$ | —OC$_8$H$_{17}$—n |
| —OCH$_3$ | —OC$_{12}$H$_{25}$—n |
| —OCH$_3$ | —OCH$_2$C$_6$H$_5$ |
| —OC$_2$H$_5$ | —OC$_6$H$_5$ |
| —OCH$_3$ | —OSi(CH$_3$)$_3$ |
| —OC$_2$H$_5$ | —OC$_2$H$_5$ |
| —OC$_3$H$_7$—iso | —OC$_3$H$_7$—iso |
| —OC$_4$H$_9$—n | —OC$_4$H$_9$—n |
| —OC$_8$H$_{17}$—n | —OC$_8$H$_{17}$—n |
| —OCH$_2$CH(C$_2$H$_5$)(CH$_2$)$_3$CH$_3$ | —OCH$_2$CH(C$_2$H$_5$)(CH$_2$)$_3$CH$_3$ |
| —OC$_{12}$H$_{25}$—n | —OC$_{12}$H$_{25}$—n |
| —OC$_6$H$_{11}$—cyclo | —OC$_6$H$_{11}$—cyclo |
| —OC$_6$H$_5$ | —OC$_6$H$_5$ |
| —OC$_6$H$_4$Cl—p | —OC$_6$H$_4$Cl—p |
| —OC$_6$H$_3$(CH$_3$)$_2$—2,4 | —OC$_6$H$_3$(CH$_3$)$_2$—2,4 |
| —OCH$_2$CH$_2$Cl | —OCH$_2$CH$_2$Cl |
| —OCH$_2$C$_6$H$_5$ | —OCH$_2$C$_6$H$_5$ |
| —OSi(CH$_3$)$_3$ | —OSi(CH$_3$)$_3$ |

TABLE 2

X is O, A is —OR', D is other than —OR'

| A | D |
|---|---|
| —OH | —n.C$_4$H$_9$ |

TABLE 2-continued

X is O, A is —OR', D is other than —OR'

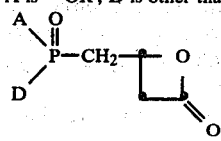

| A | D |
|---|---|
| —OCH$_3$ | —CH$_3$ |
| —OC$_4$H$_9$—iso | —CH$_3$ |
| —OC$_2$H$_5$ | —C$_2$H$_5$ |
| —OC$_4$H$_9$—n | —C$_2$H$_5$ |
| —OCH$_3$ | —CH$_2$CH$_2$Cl |
| —OC$_2$H$_5$ | —C$_6$H$_5$ |
| —OC$_2$H$_5$ | —C$_6$H$_4$Cl—p |

TABLE 3

X is O, A and D are other than —OR'

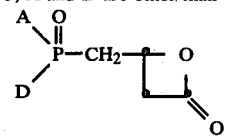

| A | D |
|---|---|
| H | —iso-C$_3$H$_7$ |
| H | —CH$_2$CH$_2$CN |
| H | —C$_6$H$_5$ |
| H | —CH$_2$—[cyclic] |
| —CH$_3$ | —CH$_3$ |
| —CH$_2$CH$_2$CN | —CH$_2$CH$_2$CN |
| —CH$_2$CH$_2$CN | —CH$_2$—[cyclic] |
| —C$_6$H$_5$ | —C$_6$H$_5$ |
| —C$_6$H$_5$ | —CH$_2$—[cyclic] |
| —CH$_2$—[cyclic] | —CH$_2$—[cyclic] |

TABLE 4

=X is absent, A and D are other than —OR'

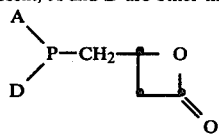

| A | D |
|---|---|
| H | H |
| H | —CH$_3$ |
| H | —CH$_2$CH$_2$CN |
| H | —C$_6$H$_5$ |

TABLE 4-continued

=X is absent, A and D are other than —OR'

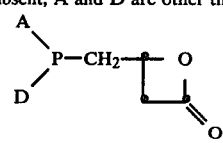

| A | D |
|---|---|
| H | —CH$_2$—[cyclic] |
| —CH$_2$CH$_2$CN | —CH$_2$CH$_2$CN |
| —CH$_2$—[cyclic] | —CH$_2$—[cyclic] |
| —C$_6$H$_5$ | —C$_6$H$_5$ |
| —C$_6$H$_5$ | —CH$_2$—[cyclic] |

TABLE 5

=X is absent, A is —OR', D is other than —OR'

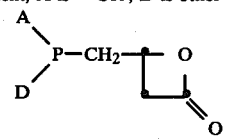

| A | D |
|---|---|
| —OCH$_3$ | —CH$_3$ |
| —OCH$_3$ | —C$_6$H$_5$ |
| —OC$_4$H$_9$—n | —CH$_3$ |

TABLE 6

=X is absent, A is —OR', D is —OR'

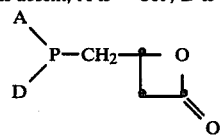

| A | D |
|---|---|
| —OCH$_3$ | —OCH$_3$ |
| —OC$_6$H$_5$ | —OC$_6$H$_5$ |

TABLE 7

X is S, A is —OR', D is —OR'

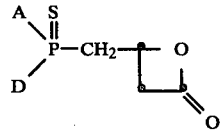

| A | D |
|---|---|
| —OCH$_3$ | —OCH$_3$ |
| —OC$_2$H$_5$ | —OC$_2$H$_5$ |
| —OC$_3$H$_7$—iso | —OC$_3$H$_7$—iso |

TABLE 7-continued

X is S, A is —OR', D is —OR'

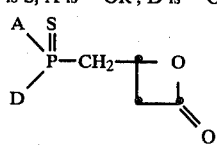

| A | D |
|---|---|
| $\underset{\|}{-OCH_2CH(CH_2)_3CH_3}^{C_2H_5}$ | $\underset{\|}{-OCH_2CH(CH_2)_3CH_3}^{C_2H_5}$ |
| —OCH$_2$CH$_2$Cl | —OCH$_2$CH$_2$Cl |

TABLE 8

X is S, A is OR', D is other than —OR'

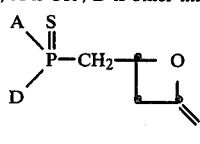

| A | D |
|---|---|
| —OCH$_3$ | —n-C$_4$H$_9$ |
| —OC$_4$H$_9$—n | —C$_6$H$_5$ |
| —OC$_6$H$_5$ | —CH$_3$ |
| —OCH$_2$C$_6$H$_5$ | —CH$_3$ |

TABLE 9

X is S, A and D are other than —OR'

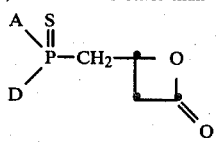

| A | D |
|---|---|
| H | —C$_6$H$_5$ |
| H | —CH$_2$—[ring O, =O] |
| —CH$_2$CH$_2$CN | —CH$_2$CH$_2$CN |
| —CH$_2$—[ring O, =O] | —CH$_2$—[ring O, =O] |
| —C$_6$H$_5$ | —C$_6$H$_5$ |

The following formulae II to VI illustrate further compounds of formula I wherein A and D together with the phosphorus atom to which they are both attached, form a 1,3,2-dioxaphospholane ring or a 1,3,2-dioxaphosphorinane ring:

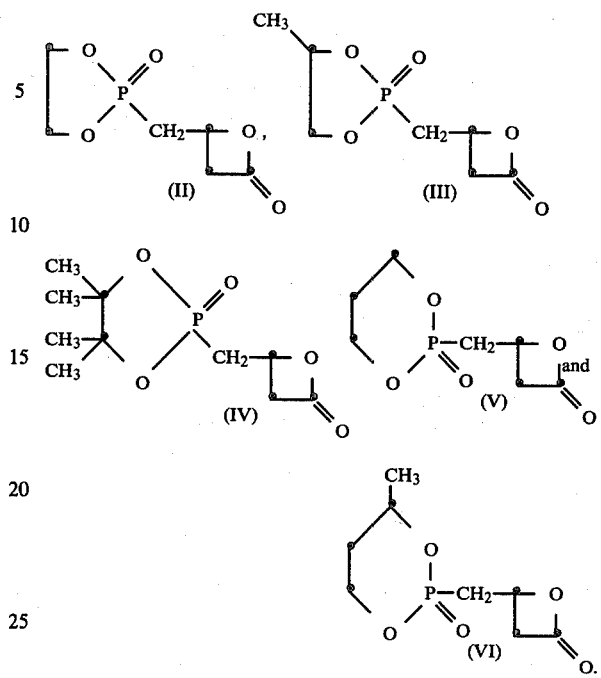

The compound types set forth in Tables 1 to 3, 7, 8 and 9 are preferred compound types; more preferred are those illustrated in Tables 1 to 3; and still more preferred are those illustrated in Tables 1 and 2.

However, compounds of formula I which are most preferred are those in which X is O, A is —OR" and D is —OR" or C$_1$-C$_3$ alkyl where R" is C$_3$-C$_7$ cycloalkyl or C$_1$-C$_{12}$ alkyl, more particularly those wherein X is O, D is C$_1$-C$_3$ alkyl, A is —OR" and R" has the aforementioned meaning. Especially preferred are compounds where X is O and A and D are the same —OR". In these preferred embodiments R" is most preferably C$_1$-C$_{12}$ alkyl.

Preferred specific compounds are: dimethyl 2-oxo-4-oxetanylmethylphosphonate, diethyl 2-oxo-4-oxetanylmethylphosphonate, di-n-butyl 2-oxo-4-oxetanylmethylphosphonate, di-n-octyl 2-oxo-4-oxetanylmethylphosphonate, di-2-ethylhexyl 2-oxo-4-oxetanylmethylphosphonate, di-ispropyl 2-oxo-4-oxetanyl-methylphosphonate, di-cyclohexyl 2-oxo-4-oxetanylmethylphosphonate, n-butyl ethyl(2-oxo-4-oxetanylmethyl)phosphinate, and isobutyl methyl(2-oxo-4-oxetanylmethyl)-phosphinate.

The present invention also provides a process of preparing a compound of formula I and salts thereof as defined which comprises reacting a compound having the formula VII

wherein A, D and X have their previous designation with diketene in the presence of an agent capable of forming free radicals, and optionally converting compounds of formula I, wherein R' is hydrogen into a salt as hereinbefore defined, in a manner known per se.

The weight ratio of the compound of formula VII to diketene may vary from 1:10 to 10:1 in the above process; when either or both A and D are hydrogen, then more than one equivalent of diketene may react with the compound of formula VII to give 2:1 and 3:1 adducts. The starting materials of formula VII are known compounds.

Examples of agents forming free radicals are as follows:
(i) Ionising radiation;
(ii) Ultraviolet radiation;
(iii) Organic peroxides e.g. t-butylperacetate, t-butylperbenzoate, acetylperoxide, benzoylperoxide, diisopropylperdicarbonate, bis-(t-butylcyclohexyl)-perdicarbonate, di-t-butylperoxide, and t-butylhydroperoxide;
(iv) Inorganic peroxy compounds e.g. hydrogen peroxide and ammonium persulphate;
(v) Organic azo compounds e.g. azobisisobutyronitrile and azobisisopropane;
(vi) Combination of (iii) or (v) with ultraviolet radiation;
(vii) Combination of (iii) or (iv) with a metal ion catalyst e.g. Cu, Ti, V, Fe ions to give a radical producing redox-system e.g.
$H_2O_2 + Fe^{2+}$
$NH_4^+ {}^-O_3S-O-O-SO_3^- NH_4^+ + Cu^+$
t-Butylhydroperoxide + $Ti^{2+}$.

Preferred agents forming free radicals are organic peroxides, organic azo compounds or combinations of an organic peroxide or of an organic azo compound with ultraviolet radiation.

The radical forming substances [(iii), (iv), (v)] may be used advantageously in catalytic amounts of 0.1–10 mol%, preferably 1–5 mol%, based on the amount used of diketene.

In the above process, one of the reactants may act as the solvent but if desired the reaction may be carried out in the presence of an inert solvent of the type conventionally used for free radical reactions, for example petroleum ether in low temperature reactions, benzene or toluene in moderate temperature reactions and chlorobenzene in high temperature reactions. The reaction may be carried out, if desired, in a gas atmosphere, e.g. nitrogen, inert under the reaction conditions. The reaction may be carried out at a temperature from −20° C. to 200° C. depending on the radical producing method employed. The preferred temperature is usually from 80° C. to 120° C. The reaction may be carried out under pressure for example when the compound of formula VII is a phosphine.

Preferably a mixture of diketene and the agent capable of forming free radicals are added to a stirred and heated excess of the phosphorous compound of formula VII, batchwise or, in a continuous manner, e.g. in a cascade reactor.

The present invention also provides a process of preparing a compound of formula I where X is oxygen or sulphur which comprises reacting the corresponding compound of formula I where X is absent with an oxidising agent or sulphur, respectively. Examples of suitable oxidising agents are hydrogen peroxide and atmospheric oxygen. This process is particularly useful when one or both A and D are hydrogen or

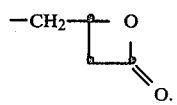

The present invention further provides a process of preparing a compound of formula I where either or both A and D are the group —R'O in which R' is hydrogen, by the hydrolysis or alcoholysis of the corresponding compound of formula I where the groups R' are trimethylsilyl. The hydrolysis may be carried out using methods well known per se e.g. under very mild conditions using stoichiometric amounts of water in a solvent at ambient temperatures in the presence or absence of a suitable cation. The alcoholysis may also be carried out at ambient temperatures using the alcohol as solvent and in the presence or absence of a suitable cation.

The compounds of formula I may be used as friction modifiers and anti-wear additives for lubricating oils, to impart flame retardancy to natural and synthetic polymers, and also as intermediates for a wide variety of chemicals such as water treatment chemicals, flame retardants, and biologically active compounds.

Accordingly, the present invention also provides a lubricant composition comprising a lubricating oil and, as friction modifier and/or antiwear additive, an effective amount of a compound of formula I as hereinbefore defined, optionally together with customary additives.

The present invention still further provides a method of imparting flame retardancy to natural and synthetic polymers in which there is used, as active ingredient, an effective amount of compound of formula I as hereinbefore defined.

The following Examples further illustrate the present invention. Parts and percentages are by weight.

EXAMPLE 1

A mixture of 84 parts of diketene and 6.5 parts of bis-(t-butylcyclohexyl)perdicarbonate was added dropwise over a period of one hour to 440 parts of dimethylphosphite and the whole was vigorously stirred at 80° C. in a nitrogen atmosphere. The temperature of the reaction mixture rose to 90° C. during the addition. On completion of the addition, the reaction mixture was heated for a further 40 minutes at 80°–90° C., then cooled to room temperature (20°–25° C.). Excess phosphite and other volatile materials were removed by means of a rotary evaporator at a pressure of 1.33 mb (millibar) and a temperature rising to 100° C. The residue was cooled and dissolved in 200 parts of ethyl acetate at room temperature. To this solution 750 parts of cyclohexane were added and the mixture stored at 0° for 18 hours. The precipitated crystalline dimethyl 2-oxo-4-oxetanylmethylphosphonate was collected, washed with cyclohexane and dried and was found to melt at 46°–47° C. A sample recrystallised from ethyl acetate had m.pt. 47°–48° C. and had the following elemental analysis by weight:

Calculated for $C_6H_{11}O_5P$ C, 37.12; H, 5.71; P, 15.95: Found C, 37.33; H, 5.98; P, 15.90.

As an alternative to recrystallisation, the crude product could be purified by distillation in a wiped wall still at a pressure of 0.26 mb and wall temperature of 140° C.

When similar reactions were carried out by reacting diketene with other phosphites under the reaction conditions, summarised in Table 10, the corresponding 2-oxo-4-oxetanylmethylphosphonate diesters were obtained after purification by distillation in a wiped wall still.

TABLE 10

Preparation of 2-oxo-4-oxetanylmethylphosphonate diesters

Phosphite $(RO)_2P\overset{O}{\underset{H}{\diagup\!\!\!\diagdown}}$

| Example | R = | Catalyst | Reaction Temperature °C. | Distillation Temp./Pressure °C. |
|---|---|---|---|---|
| 2 | $-C_2H_5$ | a | 80° | 140°/0.67 mb |
| 3 | $-n-C_4H_9$ | a | 80° | 170°/0.26 mb |
| 4 | $-n-C_8H_{17}$ | a | 80° | 170°/0.26 mb |
| 5 | $CH_3(CH_2)_3\overset{C_2H_5}{\underset{\mid}{C}}HCH_2-$ | a | 80° | 160°/0.08 mb |
| 6 | $iso-C_3H_7-$ | a | 80° | 145°/1.33 mb |
| 7 | $ClCH_2CH_2-$ | b | 120° | 75°/0.067 mb |
| 8 | $(CH_3)_3Si-$ | c | 90° | 124°/0.013 mb |
| 9 | cyclo $C_6H_{11}-$ | b | 120° | 160°/0.013 mb |

Note:
a = bis-(t-butylcyclohexyl)perdicarbonate
b = dibenzoyl peroxide
c = tert-butylperbenzoate.

EXAMPLE 10

0.36 parts of water were added to a stirred solution of 3.1 parts of bis-trimethylsilyl 2-oxo-4-oxetanylmethylphosphonate of Example 8 in 25 parts of diethylether at room temperature. After 30 minutes the ethereal layer was decanted from the precipitated oil and the oil washed twice by stirring with a little diethylether. The oil was dissolved in 25 parts of ethanol at room temperature and 0.99 parts of cyclohexylamine were added. After standing for 20 minutes the precipitated monocyclohexylamine salt of 2-oxo-4-oxetanylmethylphosphonic acid was collected, washed with ethanol and dried and had a melting point of 129°–130° C. The compound had the following elemental analysis by weight:

Calculated for $C_{10}H_{20}NO_3P$ C, 45.28; H, 7.60; N, 5.28; P, 11.68: Found C, 45.28; H, 7.95; N, 5.56; P, 11.73.

EXAMPLE 11

A mixture of 8.4 parts of diketene, 13.6 parts of a mixture of cis and trans 4-methyl-2-oxo-1,3,2-dioxaphosphorinane and 1.2 parts of benzoyl peroxide was added dropwise over a period of one hour to 54.4 parts of a mixture of cis and trans 4-methyl-2-oxo-1,3,2 dioxaphosphorinane which was stirred in an atmosphere of nitrogen and heated at 120° C. At the end of the addition, the excess phosphorinane was removed by twice passing the reaction mixture down a wiped wall molecular still, first at a wall temperature of 60° C. and then at a wall temperature of 80°, the pressure being 0.067 mb in each case. The product, a mixture of cis and trans 4-methyl-2-oxo-2-(2-oxo-4-oxetanylmethyl)-1,3,2-dioxaphosphorinane was distilled in a wiped wall molecular still at a wall temperature of 150° C. and a pressure of 0.067 mb and was obtained as a colourless, viscous oil.

EXAMPLE 12

A mixture of 30.8 parts of didodecyl phosphite, 4.2 parts of diketene and 0.6 parts of benzoyl peroxide was added dropwise over 30 minutes to 42 parts of didodecyl phosphite which was vigorously stirred at 120° C. in a nitrogen atmosphere. After completion of the addition, stirring was continued for 30 minutes, then the excess of didodecyl phosphite was removed on a wiped wall still at a temperature of 160° C. and pressure of 0.067 mb. The residue of didodecyl 2-oxo-4-oxetanyl-methylphosphonate was crystallised from n-hexane, had m.p. 51°–52.5° C. and had the following elemental analysis by weight Calculated for $C_{28}H_{55}O_5P$ C, 67.03; H, 10.85; P, 6.17: Found C, 66.82; H, 11,20; P, 5.98.

EXAMPLE 13

A mixture of 13.2 parts of dodecyl methylphosphite, 4.2 parts of diketene and 0.6 parts of bis-(t-butylcyclohexyl)-perdicarbonate was added dropwise over 30 minutes to 39.6 parts of dodecylmethylphosphite which was vigorously stirred at 85° C. in a nitrogen atmosphere. On completion of the addition the reaction mixture was heated for a further 30 minutes at 85° C., then the excess of dodecylmethylphosphite was removed on a wiped wall still at a wall temperature of 80° C. and pressure 0.013 mb. The residue was distilled on a wiped wall still at a wall temperature of 150° C. and pressure 0.013 mb, and gave dodecyl methyl 2-oxo-4-oxetanylmethylphosphonate as a colourless oil which had the following analysis by weight:

Calculated for $C_{17}H_{33}O_5P$: C, 58,60; H, 9.55; P, 8.89: Found C, 59,20; H, 9.79; P, 8.83.

EXAMPLE 14

A solution of 0.16 parts of bis-(t-butylcyclohexyl)-perdicarbonate in 2.1 parts of diketene was added dropwise over one hour to 12.6 g of dimethyl thiophosphite which was stirred at 95° C. under a nitrogen atmosphere. Infra-red examination of the reaction mixture showed that little β-lactone had been formed.

0.6 parts of benzoyl peroxide were dissolved in 2.1 parts of diketene and 2.0 parts of the reaction mixture above. This mixture was added dropwise over 1 hour to the remainder of the reaction mixture at 120° C. with vigorous stirring in a nitrogen atmosphere. Excess phosphite was distilled off at 40° C. under reduced pressure and the residue was distilled twice in a Kugelrohr at a temperature of 80° C. and a pressure of 0.067 mb to give the product, dimethyl 2-oxo-4-oxetanylmethylthiophosphonate, as an orange oil which had the following analysis by weight.

Calculated for $C_6H_{11}O_4PS$ C, 34,29; H, 5.28; P, 14.73; S, 15.25: Found C, 34.17; H, 5.27; P, 14,41; S, 15.23.

EXAMPLE 15

A mixture of 16.8 parts of diketene, 4.8 parts of benzoyl peroxide and 40.0 parts of diethyl thiophosphate was added dropwise over 1 hour to 83.3 parts of diethyl thiophosphite which was stirred at 120° C. in a nitrogen atmosphere. At the end of the reaction time, excess starting materials and volatile impurities were removed from the product by twice passing the reaction mixture down a wiped wall still, initially at 70° C. and a pressure of 20 mb, then at 45° C. and a pressure of 0.013 mb.

The product diethyl 2-oxo-4-oxetanylmethylthiophosphonate, was distilled on the wiped wall still at a temperature of 60° C. and pressure of 0.013 mb and was obtained as a mobile orange oil which had the following elemental analysis by weight.

Calculated for $C_8H_{15}O_4PS$ P, 13.00; S, 13.46; Found P, 12.84; S, 13.77.

EXAMPLE 16

A mixture of 8.4 parts of diketene, 0.25 parts of azobisisobutyronitrile and 50 parts of toluene was irradiated by a medium pressure mercury lamp at room temperature under an atmosphere of nitrogen while a slow stream of phosphine was passed into the reaction. After two hours, when approximately 3.4 parts of phosphine had been passed in, the irradiation was stopped and the flow of phosphine discontinued.

The formation of β-lactones in the reaction mixture was indicated by the appearance of an infra-red absorption at 1830 cm$^{-1}$.

A triplet at $\delta+162.3$ (J=194 Hz) in the $^{31}$P NMR spectrum of the reaction mixture confirmed the presence of 2-oxo-4-oxetanylmethylphosphine. Likewise the presence of the diastereoisomers of bis(2-oxo-4-oxetanylmethyl)phosphine was shown by two doublets in the $^{31}$P NMR spectrum at $\delta+66.7$ (J=220 Hz) and $\delta+65.0$ (J=215 Hz).

EXAMPLE 17

A mixture of 11.0 parts of phenylphosphine, 8.4 parts of diketene, 0.25 parts of azobisisobutyronitrile and 70 parts of toluene was irradiated for 5 hours at room temperature in a nitrogen atmosphere by a medium pressure mercury lamp. The crude reaction mixture was evaporated in vacuo at room temperature, then kept at 0.013 mb for two hours to remove volatile impurities. The diastereoisomeric mixture of (2-oxo-4-oxetanylmethyl)phenyl phosphine was obtained as an unstable oil having an IR spectrum characteristic of a β-lactone (C=O, λmax 1820 cm$^{-1}$) and showing two signals in the $^{31}$P NMR at $\delta+65.6$ (doublet, J=210 Hz) and $\delta+67.6$ (doublet, J=210 Hz).

EXAMPLE 18

A mixture of 2.1 parts of diketene and 0.4 parts of azobisisobutyronitrile were added dropwise over 15 minutes to 18.6 parts of diphenylphosphine which was stirred and heated at 85° C. in a nitrogen atmosphere. After the addition, the reaction mixture was heated for a further 5 minutes at 85° C., then cooled to room temperature. The excess diphenylphosphine and volatile impurities were removed by distillation on a wiped wall still at a wall temperature of 85° C. and a pressure of 0.04 mb, then the residue was distilled in the wiped wall still at 120° C. and a pressure of 0.013 mb. The product, (2-oxo-4-oxetanylmethyl)-diphenylphosphine, was obtained as a colourless oil and had an absorption at 1825 cm$^{-1}$ in the infra-red spectrum, characteristic of a β-lactone.

EXAMPLE 19

A mixture of 4.2 parts of diketene, 10.1 parts of diphenylphosphinous acid, 2.3 parts of bis-(t-butylcyclohexyl)-perdicarbonate and 70 parts of toluene was stirred by a stream of nitrogen in a quartz apparatus at room temperature while being irradiated by UV light from a medium pressure mercury lamp. After three hours irradiation, the reaction mixture was filtered, and the filtrate evaporated. The semi-crystalline residue was triturated with a little toluene, and the crystals collected on a filter and washed with toluene. Crystallisation from toluene gave colourless crystals of (2-oxo-4-oxetanylmethyl)-diphenylphosphine oxide which melted at 154°–155° C. and had the following elemental analysis by weight.

Calculated for $C_{16}H_{15}O_3P$ C, 67.13; H, 5.28; P, 10.82: Found C, 67.27; H, 5.44; P, 10.62.

EXAMPLE 20

A mixture of 9.3 parts of diphenylphosphine, 4.2 parts of diketene, 0.25 parts of azobisisobutyronitrile and 70 parts of toluene was stirred by a stream of nitrogen at room temperature while being irradiated by UV light from a medium pressure mercury lamp. After 22 hours irradiation, the reaction mixture was evaporated at room temperature under reduced pressure, and the oily residue kept at room temperature and a pressure of 0.013 mb for 1 hour to remove volatile impurities. The residue was shown to be (2-oxo-4-oxetanylmethyl)diphenylphosphine by comparison of its infra-red spectrum with that of the product in Example 18.

The crude (2-oxo-4-oxetanylmethyl)-diphenylphosphine was dissolved in toluene and a stream of air passed through for a total of 16 hours. The solution was run on to a column of silica gel and the column eluted with toluene containing increasing proportions of ethyl acetate. Final elution with methanol gave a fraction which was shown to be a mixture of diphenylphosphinous acid and (2-oxo-4-oxetanylmethyl)-diphenylphosphine oxide. Crystallisation of this fraction twice from toluene gave white crystals of pure (2-oxo-4-oxetanylmethyl)diphenylphosphine oxide identical to the product in Example 19.

EXAMPLE 21

A mixture of 0.84 parts of diketene and 0.26 parts of azobisisobutyronitrile was added dropwise to a refluxing solution of 1.25 parts of di-2-cyanoethyl-phosphinous acid in 25.0 parts of methylcyanide. After the addition the solution was evaporated under reduced pressure and the residue kept under high vacuum for 14 hours. The impure product was purified by dissolving in acetone and removing unreacted di-2-cyanoethyl-phosphinous acid by filtration. Evaporation of the acetone followed by thorough trituration of the residue with toluene gave, after drying under high vacuum, di-2-cyanoethyl-2-oxo-4-oxetanylmethylphosphine oxide as a viscous colourless oil having bands in the infra-red spectrum at 1820 cm$^{-1}$ and 2240 cm$^{-1}$ characteristic of a β-lactone and cyano group respectively.

EXAMPLE 22

A mixture of 10.9 parts of diphenylthiophosphinous acid, 4.2 parts of diketene, 1.25 parts of azobisisobutyronitrile and 70 parts of toluene was irradiated by UV light from a medium pressure mercury lamp while being stirred at room temperature by a stream of nitrogen. After 2½ hours the irradiation was stopped and the toluene evaporated. The residue was triturated with 30 parts of diethylether to give white crystals which were collected and recrystallised twice from a mixture of toluene/petroleum ether (b.p. 100°–120° C.). The product, (2-oxo-4-oxetanylmethyl)diphenylphosphine sulphide, melted at 106°–107° C. and had the following elemental analysis by weight.

Calculated for $C_{16}H_5O_2PS$ C, 63.57; H, 5.00; P, 10.24; S, 10.6: Found C, 63.49; H, 5.14; P, 9.95; S, 10.7.

EXAMPLE 23

A solution of 0.98 parts of bis-(t-butylcyclohexyl)perdicarbonate in 12.6 parts of diketene was added dropwise over 1 hour to 90.2 parts of n-butyl ethylphosphonite which was vigorously stirred at 85° C. in a nitrogen atmosphere. After the addition the reaction mixture was passed down a wiped wall still at a temperature of 50°

C. and a pressure of 0.13 mb to remove the excess phosphonite. The residue was distilled on the wiped wall still at a temperature of 75° C. and a pressure of 0.013 mb. The product n-butyl ethyl(2-oxo-4-oxetanylmethyl)-phosphinate, was obtained as a colourless oil which the $^{31}$P NMR showed to be a nearly equal mixture of diastereoisomers having chemical shifts of $\delta-52.4$ and $\delta-52.7$ and which had the following elemental analysis by weight.

Calculated for $C_{10}H_{19}O_4P$ C, 51.28; H, 8.18; P, 13.22: Found C, 51.73; H, 8.44; P, 13.43.

EXAMPLE 24

A mixture of 8.4 parts of diketene, 2.5 parts of benzoyl peroxide and 20.0 parts of ethyl phenylphosponite were added dropwise over 1 hr to 48.1 parts of vigorously stirred ethyl phenylphosphonite which was heated at 120° C. in an atmosphere of nitrogen. The excess phosphonite was removed by passing the reaction mixture down a wiped wall still at 80° C. at a pressure of 0.013 mb. The residue was distilled on a wiped wall still at a temperature of 110° C. and a pressure of 0.013 mb and the product, ethyl(2-oxo-4-oxetanylmethyl)phenylphosphinate, was obtained as a colourless oil which was shown by $^{31}$P NMR to be a nearly equal mixture of diastereoisomers having chemical shifts at $\delta-37.5$ and $\delta-37.7$ and which had the following elemental analysis by weight.

Calculated for $C_{12}H_{15}O_4P$ C, 56.69; H, 5.95; P, 12.18: Found C, 56.15; H, 6.25; P, 12.06.

EXAMPLE 25

A mixture of 7.4 parts of diketene and 1.2 parts of bis-(t-butylcyclohexyl)-perdicarbonate was added dropwise over 1 hour to 65.4 parts of vigorously stirred n-butyl phenylthiophosphonite which was heated at 85° C. in a nitrogen atmosphere. The mixture was then passed down a wiped wall still at 70° C. and a pressure of 0.013 mb to remove unreacted starting materials. The residue was distilled on the wiped wall still at 115° C. and a pressure of 0.013 mb and gave crude n-butyl(2-oxo-4-oxetanylmethyl)phenylthiophosphinate as a colourless oil which contained a more volatile impurity. The crude product was passed down a wiped wall still at 85° C. and a pressure of 0.013 mb and the involatile fraction was found to be pure n-butyl(2-oxo-4-oxetanylmethyl)phenylthiophosphinate which $^{31}$P NMR showed to be a mixture of diastereoisomers having chemical shifts at $\delta-83.7$ and $\delta-83.2$ and which had the following elemental analysis by weight.

Calculated for $C_{12}H_{15}O_3P$ C, 56,36; H, 6.42; S, 10.75: Found C, 56.21; H, 6.41; S, 10.38.

EXAMPLE 26

A mixture of 4.2 parts of diketene and 0.33 parts of bis-(t-butylcyclohexyl)perdicarbonate was added dropwise over 1 hour to 27.2 parts of vigorously stirred isobutyl methylphosphonite which was heated at 85° in a nitrogen atmosphere. After the addition the reaction mixture was passed down a wiped-wall still at a temperature of 50° C. and a pressure of 0.13 mb to remove the excess phosphonite. The residue was distilled on the wiped wall still at a temperature of 75° and a pressure of 0.13 mb. The product isobutyl methyl(2-oxo-4-oxetanylmethyl)phosphinate was obtained as a colourless oil with a characteristic infra-red band at 1820 cm$^{-1}$.

EXAMPLES 27–30

Antiwear Activity

Using the Shell 4-ball extreme pressure tester, the following characteristics were determined (IP 239/73 Tentative)

(i) initial seizure load (I.S.L.) which is the applied load at which the oil film first breaks down within a period of 10 seconds.

(ii) scar diameter after a load of 70 kg. has been applied for one hour with the oil initially at ambient temperature.

The lubricant used was an SAE 30 grade oil having a viscosity of 116 CS at 100° F. The results of the test are summarized in the following Table 11.

TABLE 11

Antiwear Activity of Compounds of the Invention

| Example | Additive used | Additive Concentration % w/w | ISL (Kg.) | Scar Diam. (mm) at 70 Kg load |
|---|---|---|---|---|
| 27 | None | | 60 | 2.42 |
| 28 | Product of Ex. 1 | 0.5 | 110 | 0.75 |
| 29 | Product of Ex. 4 | 1.0 | 130 | 0.68 |
| 30 | Product of Ex. 5 | 1.0 | 130 | 0.76 |

EXAMPLE 31

Flame-retarding Effect on Cotton Fabric

A piece of cotton fabric was treated as follows:
Immersed for 5 minutes in cold 15% NaOH;
Rinsed for 1 minute cold and squeezed out;
Immersed for 5 minutes in a 30% aqueous solution of the product of Example 1 at 5° C.;
Rinsed for 5 minutes in boiling water;
Neutralised for 5 minutes with 5 ml/liter 40% acetic acid;
Rinsed cold, squeezed out and dried.
The cotton fabric had acceptable handling and showed no loss of strength.
The phosphorous incorporation was approximately 3%.
The treated cotton fabric showed a substantial flame retarding effect.

What we claim is:

1. A compound having the formula I

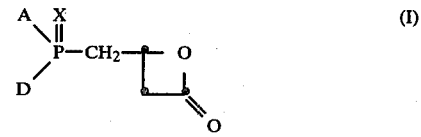

wherein X is oxygen or sulphur or the moiety X is absent; and A and D are the same or different and each is hydrogen $C_1$–$C_{12}$ straight chain or branched chain alkyl, optionally substituted by one or two halogen atoms or by a cyano, $C_1$–$C_3$ alkoxy, or $C_2$–$C_4$ alkoxycarbonyl, $C_3$–$C_7$ cycloalkyl, $C_7$–$C_{10}$ aralkyl or a phenyl group, optionally substituted by one or two halogen, cyano, $C_1$–$C_3$ alkoxy, $C_2$–$C_4$ alkoxycarbonyl or $C_1$–$C_4$ straight chain or branched chain alkyl groups, the group

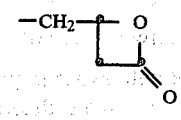

or a group R'O— wherein R' is hydrogen, a $C_1$-$C_{12}$ straight or branched chain alkyl group, optionally substituted by one or two halogen atoms, $C_3$-$C_7$ cycloalkyl, $C_7$-$C_{10}$ aralkyl, a phenyl group, optionally substituted by one or two halogen atoms or $C_1$-$C_4$ straight chain or branched chain alkyl groups, or R' is a trimethylsilyl group; or A and D together with the phosphorus atom to which they are each attached form a 1,3,2-dioxaphospholane ring or a 1,3,2-dioxaphosphorinane ring, each optionally substituted by one or more $C_1$-$C_3$ straight chain or branched chain alkyl; and where R' is hydrogen, the alkali, alkaline earth and amine salts and partial salts thereof; with the proviso that when A is the group R'O— and X is sulphur or absent then D cannot be hydrogen or the group

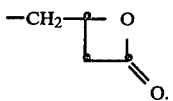

2. A compound as claimed in claim 1 wherein X is O or S.

3. A compound as claimed in claim 1 wherein X is O.

4. A compound as claimed in claim 1 wherein X is O, A is —OR' and R' is as defined in claim 1.

5. A compound as claimed in claim 1 wherein X is O, A is —OR'' and D is —OR'' or $C_1$-$C_3$ alkyl wherein R'' is $C_3$-$C_7$ cycloalkyl or $C_1$-$C_{12}$ alkyl.

6. A compound as claimed in claim 1 wherein X is O, D is $C_1$-$C_3$ alkyl and A is —OR'' wherein R'' is $C_3$-$C_7$ cycloalkyl or $C_1$-$C_{12}$ alkyl.

7. A compound as claimed in claim 1 wherein X is O, A and D are the same group —OR'' wherein R'' is $C_3$-$C_7$ cycloalkyl or $C_1$-$C_{12}$ alkyl.

8. A compound as claimed in claim 5,6 or 7 wherein R'' is an alkyl group containing 1-12 carbon atoms.

9. A compound as claimed in claim 1 selected from the group consisting of dimethyl 2-oxo-4-oxetanylmethylphosphonate, diethyl 2-oxo-4-oxetanylmethylphosphonate, di-n-butyl 2-oxo-4-oxetanylmethylphosphonate, di-n-octyl 2-oxo-4-oxetanylmethylphosphonate, di-2-ethylhexyl 2-oxo-4-oxetanylmethylphosphonate, di-isopropyl 2-oxo-4-oxetanylmethylphosphonate, di-cyclohexyl 2-oxo-4-oxetanylmethylphosphonate, n-butyl ethyl(2-oxo-4-oxetanylmethyl)phosphinate, and isobutyl methyl-(2-oxo-4-oxetanylmethyl)phosphinate.

10. A process of producing a compound of formula I or salts thereof as claimed in claim 1, comprising reacting a compound of formula VII

wherein A, D and X are as defined in claim 1, with diketene in the presence of an agent capable of forming free radicals, and optionally converting compounds of formula I wherein R' is hydrogen into a salt as defined in claim 1.

11. A process as claimed in claim 10 wherein the agent capable of forming free radicals is selected from the group consisting of an organic peroxide; an organic azo compound; or a combination of an organic peroxide or an organic azo compound with ultraviolet radiation.

12. A process as claimed in claim 10 which is carried out in a continuous manner.

13. A lubricant composition comprising a lubricating oil and, as friction modifier, an effective amount of a compound of formula I as defined in claim 1.

14. A lubricant composition comprising a lubricating oil and, as an antiwear additive, an effective amount of a compound of formula I as defined in claim 1.

* * * * *